US010334163B2

(12) United States Patent
Cogal et al.

(10) Patent No.: US 10,334,163 B2
(45) Date of Patent: Jun. 25, 2019

(54) LARGE FIELD OF VIEW MULTI-CAMERA ENDOSCOPIC APPARATUS WITH OMNI-DIRECTIONAL ILLUMINATION

(71) Applicant: ECOLE POLYTECHNIQUE FEDERALE DE LAUSANNE (EPFL), Lausanne (CH)

(72) Inventors: Ömer Cogal, Zürich (CH); Yusuf Leblebici, Lutry (CH)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 17 days.

(21) Appl. No.: 15/120,527

(22) PCT Filed: Feb. 24, 2015

(86) PCT No.: PCT/IB2015/051379
§ 371 (c)(1),
(2) Date: Aug. 22, 2016

(87) PCT Pub. No.: WO2015/128801
PCT Pub. Date: Sep. 3, 2015

(65) Prior Publication Data
US 2017/0013193 A1  Jan. 12, 2017

(30) Foreign Application Priority Data

Feb. 26, 2014 (WO) .................. PCT/IB2014/059273
Feb. 27, 2014 (WO) .................. PCT/IB2014/059299

(51) Int. Cl.
*H04N 5/232* (2006.01)
*A61B 1/00* (2006.01)
(Continued)

(52) U.S. Cl.
CPC ..... *H04N 5/23238* (2013.01); *A61B 1/00009* (2013.01); *A61B 1/00181* (2013.01);
(Continued)

(58) Field of Classification Search
CPC .... H04N 5/23238; H04N 5/247; H04N 5/243; H04N 5/2252; H04N 5/2352;
(Continued)

(56) References Cited

U.S. PATENT DOCUMENTS 3,971,065 A  7/1976 Bayer
5,425,123 A  6/1995 Hicks
(Continued)

FOREIGN PATENT DOCUMENTS

EP  2412290 A1  2/2012
JP  2006068109 A  3/2006
WO  WO2012056437 A1  5/2012

OTHER PUBLICATIONS

Camera Calibration Toolbox for Matlab, Oct. 14, 2015, retrieved from http://www.vision.caltech.edu/bouguetj/calib_doc/ on Aug. 19, 2016.
(Continued)

*Primary Examiner* — Tat C Chio
(74) *Attorney, Agent, or Firm* — Andre Roland S.A.; Nikolaus Schibli

(57) ABSTRACT

A multi-camera hemispherical very wide field of view imaging apparatus with omnidirectional illumination capability comprises a cylindrical body (4, 4.*a*, 4.*b*), a hemispherical mechanical frame (2) arranged on one end of the cylindrical body (4, 4.*a*, 4.*b*), a plurality of imaging channels (3), each imaging channel (3) comprising at least an image sensor and related optics with a fixed focus appropriate for endoscopic imaging, the plurality of imaging channels (3)
(Continued)

being distributed over the hemispherical mechanical frame (2), a light source arranged center-down at a back part of the plurality of imaging channels (3) and inside or at the end of the cylindrical body (4, 4.a, 4.b). Each imaging channel (3) comprises a plurality of lightning channels (1) around their center, each of the plurality of lightning channels (1) comprising at least one microfiber light guide having a determined angle of curvature arranged to transmit the light from the light source. The imaging apparatus further comprises a control and processing circuit (5) comprising a camera control unit (6), an illumination control unit (7), an illumination unit (8), a sample and capture unit (9), an image processing unit (10) and an output interface (11) to a PC. The camera control unit (6) is configured to power each of the plurality of imaging channels (3) and make automatic gain compensation for each imaging channel (3), the illumination control unit (7) is configured for automatic intensity dimming, the sample and capture unit (9) is an interface circuit for correct sampling, extraction and capturing frames of individual imaging channels (3), the image processing unit (10) is configured for constructing a spherical panoramic image by applying a determined algorithm, and the output interface (11) is arranged to output the spherical panoramic image to a system configured to visualize it.

11 Claims, 4 Drawing Sheets

(51) Int. Cl.
| | | |
|---|---|---|
| A61B 1/04 | (2006.01) | |
| A61B 1/05 | (2006.01) | |
| A61B 1/07 | (2006.01) | |
| G06T 3/40 | (2006.01) | |
| H04N 5/225 | (2006.01) | |
| G03B 15/03 | (2006.01) | |
| G03B 37/00 | (2006.01) | |
| H04N 5/235 | (2006.01) | |
| H04N 5/243 | (2006.01) | |
| H04N 5/247 | (2006.01) | |
| A61B 1/045 | (2006.01) | |
| G03B 37/04 | (2006.01) | |

(52) U.S. Cl.
CPC .............. *A61B 1/041* (2013.01); *A61B 1/045* (2013.01); *A61B 1/051* (2013.01); *A61B 1/07* (2013.01); *G03B 15/03* (2013.01); *G03B 37/005* (2013.01); *G06T 3/4015* (2013.01); *G06T 3/4038* (2013.01); *H04N 5/2252* (2013.01); *H04N 5/2256* (2013.01); *H04N 5/2352* (2013.01); *H04N 5/2354* (2013.01); *H04N 5/243* (2013.01); *H04N 5/247* (2013.01); *G03B 37/04* (2013.01); *H04N 2005/2255* (2013.01)

(58) Field of Classification Search
CPC .............. H04N 5/2354; H04N 5/2256; H04N 2005/2255; G03B 37/005; G03B 15/03; G03B 37/04; G06T 3/4015; G06T 3/4038; A61B 1/07; A61B 1/051; A61B 1/041; A61B 1/00181; A61B 1/00009
See application file for complete search history.

(56) References Cited

U.S. PATENT DOCUMENTS

| | | |
|---|---|---|
| 5,657,073 A | 8/1997 | Henley |
| 5,776,049 A | 7/1998 | Takahashi |
| 6,201,574 B1 | 3/2001 | Martin |
| 6,471,642 B1 | 10/2002 | Igarashi |
| 6,997,871 B2 | 2/2006 | Sonnenschein et al. |
| 7,044,908 B1 | 5/2006 | Montalbo et al. |
| 7,244,229 B2 | 7/2007 | Yokoi et al. |
| 7,662,093 B2 | 2/2010 | Gilad et al. |
| 7,869,856 B2 | 1/2011 | Refael et al. |
| 7,877,134 B2 | 1/2011 | Glukhovsky |
| 8,382,658 B2 | 2/2013 | Shigemori |
| 8,414,474 B2 | 4/2013 | Chen |
| 2002/0109774 A1* | 8/2002 | Meron ............... A61B 1/00096 348/74 |
| 2003/0174208 A1 | 9/2003 | Glukhovsky et al. |
| 2004/0257438 A1* | 12/2004 | Doguchi ............ A61B 1/00009 348/65 |
| 2009/0326321 A1 | 1/2009 | Jacobsen et al. |
| 2009/0240108 A1* | 9/2009 | Shimizu ................. A61B 1/041 600/109 |
| 2009/0306474 A1* | 12/2009 | Wilson .................... A61B 1/041 600/109 |
| 2014/0022336 A1 | 1/2014 | Ou-Yang et al. |
| 2014/0316207 A1* | 10/2014 | Hain ................. A61B 1/00073 600/194 |

OTHER PUBLICATIONS

International Search Report of PCT/IB2015/051379 dated Sep. 1, 2015.
Written Opinion of the International Search Authority dated Sep. 1, 2015.

* cited by examiner

LARGE FIELD OF VIEW MULTI-CAMERA ENDOSCOPIC APPARATUS WITH OMNI-DIRECTIONAL ILLUMINATION

CROSS REFERENCE TO RELATED APPLICATIONS

The present application is a United States national stage application of International patent application PCT/IB2015/051379 filed on Feb. 24, 2015 that designated the United States, and claims foreign priority to International patent application PCT/IB2014/059299 filed on Feb. 27, 2014, and also claims foreign priority to International patent application PCT/IB2014/059273 filed on Feb. 26, 2014, the contents of all three documents being herewith incorporated by reference in their entirety.

TECHNICAL FIELD

The invention generally concerns a multi-camera imaging apparatus. In particular, the present invention relates to a multi-camera, large field of view apparatus to be used in especially endoscopic applications. The present invention also relates to the real-time image processing system that is responsible of generating panoramic or stitched image from the multiple camera inputs.

BACKGROUND

Today conventional endoscope systems are capable of forward viewing with around 170°×60° field of view (FOV). There are disclosure like U.S. Pat. No. 8,419,630 B2, US 20110196200A1 to extend the field of view using pure optical methods. The present invention is using a multi-camera approach which is mimicking insect eyes. By this way, the presented invention aims a wide angle of view, uniform resolution, and high resolution imager for especially endoscopic applications.

SUMMARY OF INVENTION

In a first aspect the invention provides a multi-camera hemispherical very wide field of view imaging apparatus with omnidirectional illumination capability. The apparatus comprises a cylindrical body, a hemispherical mechanical frame arranged on one end of the cylindrical body, a plurality of imaging channels, each imaging channel comprising at least an image sensor and related optics with a fixed focus appropriate for endoscopic imaging, the plurality of imaging channels being distributed over the hemispherical mechanical frame, a light source arranged centre-down at a back part of the plurality of imaging channels and inside or at the end of the cylindrical body. Each imaging channel comprises a plurality of lightning channels around their centre, each of the plurality of lightning channels comprising at least one microfiber light guide having a determined angle of curvature arranged to transmit the light from the light source. The imaging apparatus further comprises a control and processing circuit comprising a camera control unit, an illumination control unit, an illumination unit, a sample and capture unit, an image processing unit and an output interface to a PC. The camera control unit is configured to power each of the plurality of imaging channels and make automatic gain compensation for each imaging channel, the illumination control unit is configured for automatic intensity dimming, the sample and capture unit is an interface circuit for correct sampling, extraction and capturing frames of individual imaging channels, the image processing unit is configured for constructing a spherical panoramic image by applying a determined algorithm, and the output interface is arranged to output the spherical panoramic image to a system configured to visualize it.

In a second aspect, the invention provides a method for distributing imaging channels over a hemispherical mechanical frame of a very wide field of view imaging apparatus The method comprises defining a first distance departing from a centre of the hemispherical mechanical frame, smaller than or equal to a second distance at which an object to be viewed is separated from the centre of the hemispherical mechanical frame, generating a virtual hemisphere and making an equal area tessellation on this virtual hemisphere with an arbitrary number of imaging directions, whereby a centre of the virtual hemisphere corresponds to the centre of the hemispherical mechanical frame, and a radius of the virtual hemisphere is equal to the first distance, where the equal area tessellation comprises dividing a surface of the virtual hemisphere into the arbitrary number of equal sized surface areas. The equal area tessellation comprises starting with the arbitrary number of imaging directions located respectively at a centre of a corresponding one of the equal sized surface areas, and iteratively checking if a coverage of the first distance is achieved by adding or subtracting one imaging direction to the tessellation at each iteration. The checking comprises ensuring that a single imaging channel angle of view is greater than or equal to a maximum radial distance on the virtual hemisphere, inside any of the equal sized tessellation areas, the angle of view of the imaging channels being assumed as constraints dictated by the optics of the imaging channels chosen to be used. The method for distributing imaging channels further comprises, when the coverage of the first distance is achieved, stopping the iterative checking and fixing all the imaging directions used in the last iterative checking as a set of locations, whereby each location corresponds to a centre of a tessellation cell on the virtual hemisphere, and back projecting the locations from the virtual hemisphere to the hemispherical mechanical frame thereby obtaining the distribution of the imaging channels on the hemispherical mechanical frame.

In a third aspect the invention provides a method for constructing a final panoramic image, comprising, generating an output as a panoramic Bayer Pattern image and converting this image to a full-colour image, whereby each pixel of the resulting panoramic Bayer pattern image represents an intensity value of a colour channel of either red or green or blue wavelength, whereby the sequence of the colour channels on the Bayer pattern is any known Bayer pattern, the intensity value of each pixel being a combination of sampled intensity values of real image sensors of imaging channels placed on a hemispherical frame, each combination being based on a selection of candidate intensity values of the real image sensors of the imaging channels on the hemispherical mechanical frame, and a Bayer Pattern representation of the images is used during the selection of the intensity value candidates for each combination to generate each panoramic pixel intensity value.

In a preferred embodiment any Bayer pattern sequence is accepted as image sensors' Bayer pattern images.

In a further preferred embodiment the selection of intensity values for each combination is determined by a trigonometric relation of a final panorama pixel viewing direction and an imaging channel sampling direction.

In a further preferred embodiment a panorama pixel viewing direction is defined as a vector starting from the centre of the hemispherical mechanical frame and directed through a point in the space at infinite proximity.

In a further preferred embodiment each panorama pixel direction is unique and not coincident.

In a further preferred embodiment each imaging channel's viewing direction is determined by using its placement and orientation on the hemispherical mechanical frame.

In a further preferred embodiment precise relative direction vectors of all the imaging channels with respect to the hemispherical mechanical frame centre are determined afterwards by using a calibration process with a calibration checker board.

In a further preferred embodiment the Bayer Pattern Panorama is demosaiced after it is generated by an image processing unit and is converted to a full colour image by using a means of interpolation method by the image processing unit.

In a further preferred embodiment the interpolation method takes into account the object boundaries in the image.

BRIEF DESCRIPTION OF THE FIGURES

The invention will be better understood in view of the description of examples of preferred embodiments and in reference to the figures, wherein.

DESCRIPTION OF THE INVENTION

The invention generally concerns a multi-camera hemispherical very wide field of view imaging apparatus with omnidirectional illumination capability. Beyond the earlier endoscopic imaging systems which either belong to optical large angle lens—single image sensor combinations or planar multi image sensor types, the inventive imaging apparatus offers a hemi-spherically placed multi camera imaging apparatus. Important features of the inventive imaging apparatus that distinguish it from the previous counterparts at least comprise: 360°×90° degree FOV imaging capability with relatively high resolution and uniform resolution imaging capability, imaging direction selection capability, and fiber-optic omni-directional illumination distribution ability.

Figure 1:
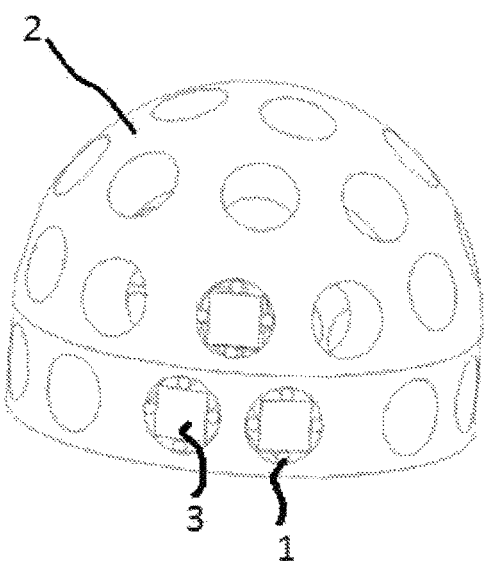
FIG. 1 illustrates an example assembly of a multi-camera dome with imaging channels and illumination channels according to the invention.
Figure 2:
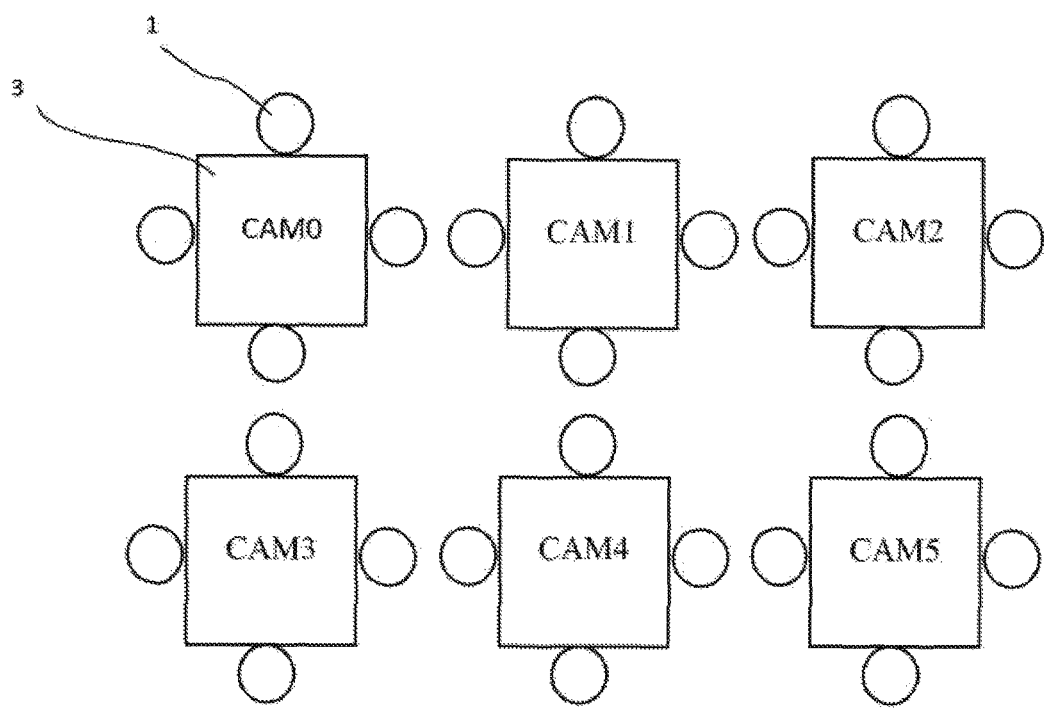
FIG. 2 contains an unrolled view of the illustration in FIG. 1 for a part of the imaging apparatus, where 6 cameras and the related illumination channels are shown.

The general structure of example embodiments of the inventive imaging apparatus are illustrated in FIG. 1 and FIG. 2. In FIG. 1, a possible way of placing imaging channels 3 on a hemispherical frame 2 with the illumination channels 1 is illustrated. Square shaped components in holes on the hemispherical frame 2 represent imaging channels 3. The imaging channels 3, may be preferably cameras comprising a lens—not illustrated in the figures—, and an image sensor—also not illustrated in the figures—. Relatively small cylindrical components illustrate the illumination channels 1. Imaging channels 1, may be preferably microfiber light guides. In FIG. 2, an unrolled portion of the hemispherical frame 2 from FIG. 1 is illustrated to visually explain how the cameras 3 and the illumination channels 1 are arranged. An illumination source—not illustrated in the figures—may be remotely connected to the illumination channels 1, therefore the illumination channels 1, will be starting from the illumination source and ending at the surface of the hemispherical frame 2. In FIG. 1, the illumination channels 1 are attached at the zero proximity of the imaging channels 3 for simplicity and better illumination. In a further preferred embodiment illustrated in FIG. 3, there is another way of distributing the illumination channels 1 independent from the imaging channels 3. In that case there will be additional holes for illumination channels on the hemispherical frame 2 distributed uniformly and in a sense to fill all the surface of the hemispherical frame 2 that is available after placement of the imaging channels 3. The case illustrated in FIG. 3 may be implemented in case of manufacturing restrictions.

The proposed device aims to provide a very wide field of view, preferably 360°×90°, as a multi-camera endoscopic imaging system. The main part of the whole system is described below.

1. Multichannel Imagers
i. Each imaging channel 3 is composed of an image sensor and related optics with a fixed focus appropriate for endoscopic imaging.
ii. The distribution of the imaging channels 3 is as described above and the steps can be listed as below:
  a) Determine the distance for full coverage desired as a first distance.
  b) Generate the virtual hemisphere at the determined first distance at step 1.ii.a) and make an equal area tessellation on this virtual hemisphere.
  c) For the tessellation; each tessellation has a number of cells, which corresponds to a surface area portion on the total surface of the virtual hemisphere. The number of the cells are equal to number of imaging channels 3. Then, start with a number of imaging channels 3, and iteratively check if the coverage of the surface area of the virtual hemisphere is achieved by adding (or maybe subtracting) 1 imaging channel 3 each iteration. The coverage can be ensured as follows: the centre of the viewing direction of each imaging channel 3 is coincident with centre of one unique tessellation cell. Each cell is mapped to the one unique imaging channel 3. If all the points of the cell is within a circle that has radial diameter equal to the angle of view of imaging channel 3, then the area portion occupied by the related cell is said to be totally covered. If all the cells are totally covered, it is said to be full coverage of the virtual hemisphere achieved.
  d) When the full coverage of the virtual hemisphere is achieved, stop the iterations and back project the centre of tessellation cells on the actual hemispherical frame 2. These are the imaging channel 3 positions.
  e) Make a validation in terms physical aspects. If there is and inconsistency, turn back to the step 1.i.a) with the information from step 1.i.e). This means to tell how much we are offset from the physical needs and then fix the tessellation centres for the cameras that are physically bounded then make the placements optimization for the rest of the tessellation cell centres. Then continue with new validation until the placement is achieved in terms of both coverage distance and physical constraints.

iii. In international publication WO2012056437A1, a placement for the cameras on a spherical surface is described in a layer by layer basis. This kind of arrangement becomes inefficient for a device that is miniaturized for applications like endoscopy. The surface area and the volume of the hemispherical mechanical frame is a bounding criteria for the number and the locations of the cameras. The present invention discloses a method especially for miniaturized applications like endoscopy by this way.

2. Multichannel Fibre-Light Guides i. Source of light is at the centre-down cylindrical part 4 of the apparatus (can be 1 or more LEDs or other means of light) and will be at a remote position.

ii. Imaging channels 1 will have an appropriate angle of curvature to distribute the light sufficiently.

iii. Each imaging channel 3 (image sensor with optics) will have four or more illumination channels 1 around.

iv. Each illumination channel 1 may have more than one micro-fiber light guide or the diameter of the fiber light guide may be varied accordingly to have sufficient light. The surface area and inner volume of the apparatus is a bounding criteria for the amount and the size of the micro-fiber light guides.

v. As stated above in the description of the invention section, second paragraph and illustrated in FIG. 3, another implementation method involves distributing sufficient number of illumination channels 1 on the hemispherical mechanical frame 2 independent from the imaging channels 3.

vi. In international publication WO2012056437A1 a general system is described for different imaging applications, however there are no means of illumination or illumination channels since the mentioned system is not proposed for endoscopic application specifically. Here we consider endoscopic applications where the illumination channels are crucial and have a high importance.

3. Control and Processing Circuit

Figure 5:
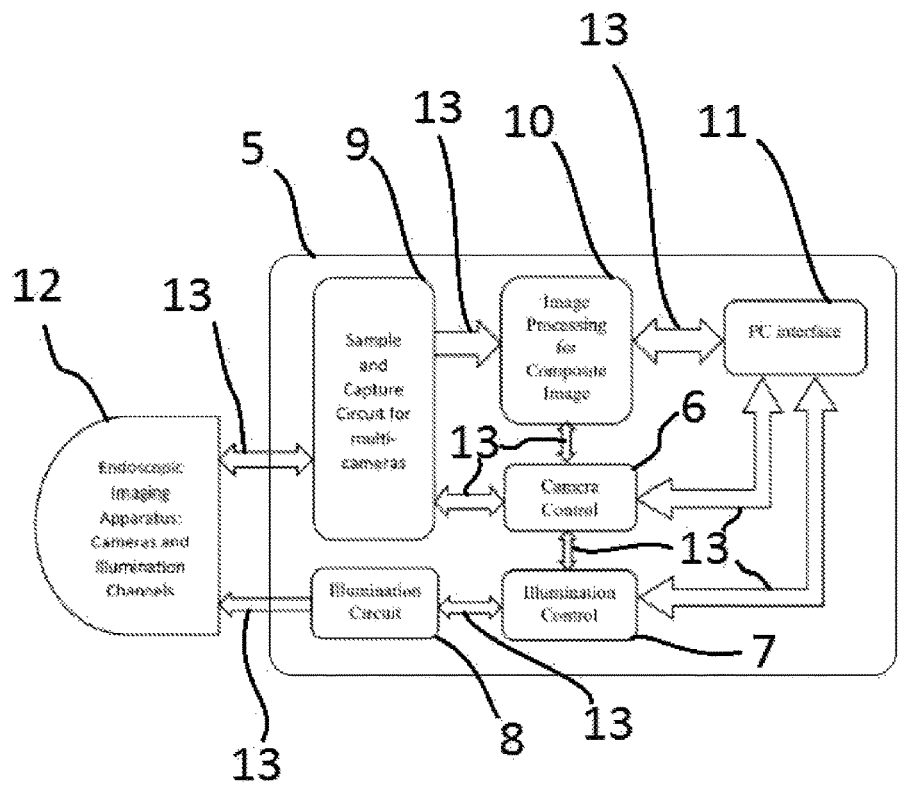
FIG. 5 schematically illustrates a control and image processing circuit for endoscopic imaging apparatus.

The control and processing circuit 5 is illustrated in FIG. 5 and has following tasks:

i. Camera Control 6: Power on off the imaging channels 3 (with different patterns for still image capturing or same time for synchronised video capturing) Make automatic gain compensation for each imaging channel 3.

ii. Illumination Control 7 and Illumination Circuit 8: Combined with the feed-back from imaging channel 3 images, make automatic intensity dimming for illumination channels 1.

iii. Sample and capture circuit for multi-cameras 9: Interface circuit for correct sampling extraction and capturing as Bayer pattern frames of individual imaging channel 3.

iv. Image processing for composite image 10: Applying the below described algorithm in description of invention section 4, create composite spherical panoramic image.

v. PC Interface 11: Interfacing via a standard bus (such as Ethernet, PCIe, HDMI . . . etc) sends the needed information to a PC environment (not represented in the figure).

vi. Endoscopic Imaging Apparatus: cameras and imaging channels 12: Is representing the apparatus composed of the hemispherical frame 2, imaging channels 3, and the illumination channels 1.

The arrows 13, in the FIG. 5 is for indicating the data flow among the control and processing unit 5, and the Endoscopic imaging apparatus 12 as well.

4. True Colour Panorama Image Processing Circuit

This algorithmic technique is based on the omega vector generation technique introduced previously in international publication WO2012056437A1. The block diagram of the control and processing circuit that will be realizing the algorithmic technique is illustrated in FIG. 5.

The main difference from previous approaches and benefits: for each imaging direction of the final panoramic image there is another degree of freedom that is the colour component of the direction. In this scheme, we have just one colour component (R/G/B) for each direction. By this way there will be a Bayer pattern for the final panorama. This Bayer pattern will be used to interpolate the final RGB panorama in one Bayer-to-RGB step. By this way the Bayer-to-RGB conversion at camera level for each camera is avoided. For circuit implementation, this eliminates the hardware cost of the individual Bayer-to-RGB conversion circuit for each camera output. This brings a significant resource saving especially when number of cameras grows. Also the colour and resolution quality of the final panorama will be improved since the sampled unprocessed true intensity inputs of the sensors are used at the final panorama construction step. That is why this technique is called "multi-camera true-colour panorama demosaicing" in this document. For endoscopic image processing applications such as bleeding detection and cancer tissue detection, real colour values have importance as features of the observed objects inside the body and colour processing capability is an important feature as well. By using high precision Bayer data instead of pre-processed colour data from the image sensor it is also aimed to achieve high precision colour processing for future applications desired in endoscopic imaging.

The steps of the implemented method are as follows:

An output is generated as a panoramic Bayer Pattern image and this image is converted to a full-colour image.

Figure 6:
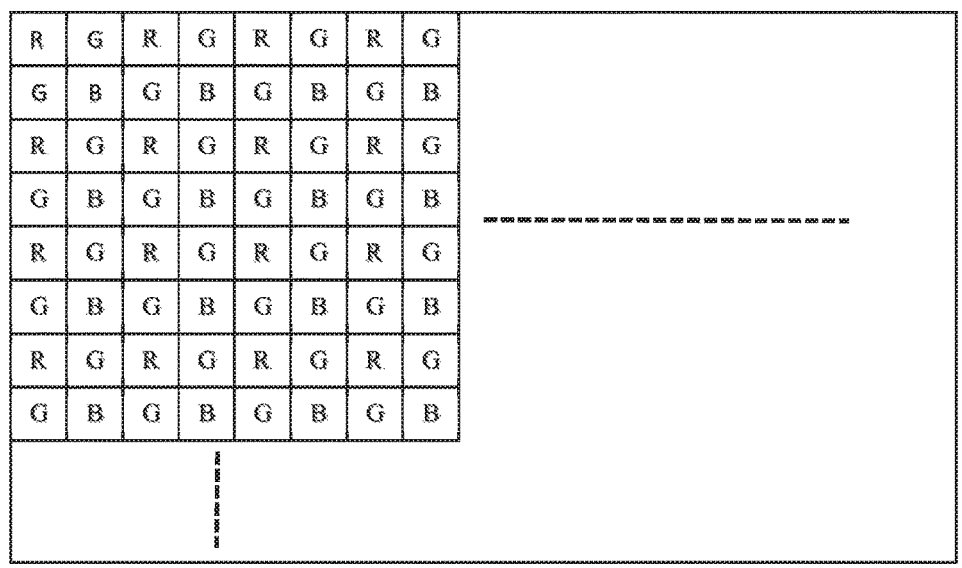
FIG. 6 contains a Final Bayer Pattern Panoramic Image representation.
Figure 7:
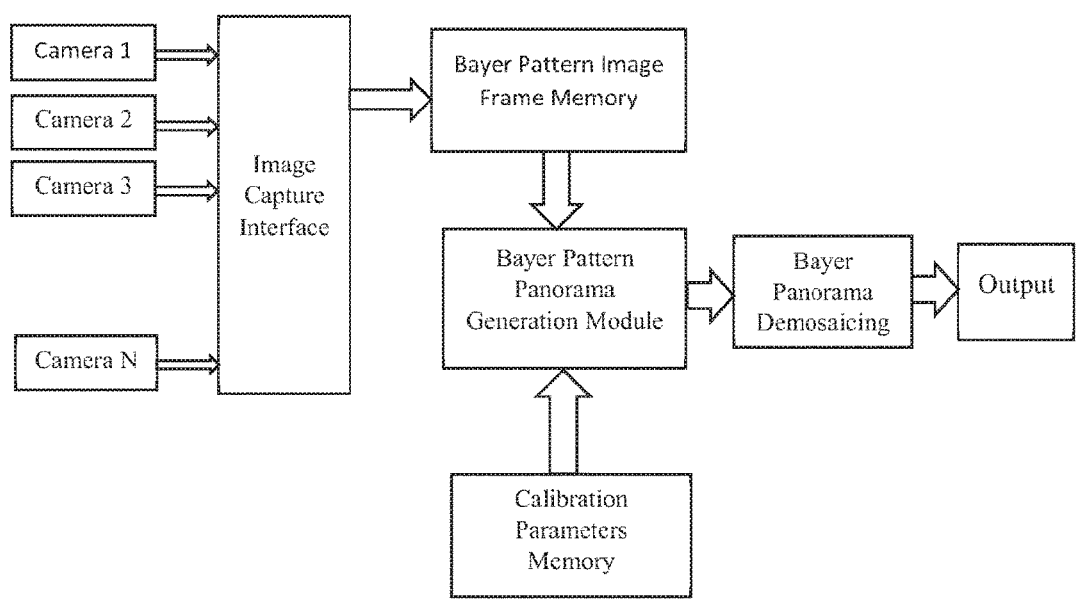
FIG. 7 contains a block diagram for a multi-camera true-colour panorama generation.

Each pixel of the resulting panoramic Bayer pattern image as illustrated in FIG. 6 represents an intensity value of a colour channel of either red or green or blue wavelength.

The sequence of the colour channels on the Bayer pattern may be any known Bayer pattern as described in reference [2].

Figure 3:
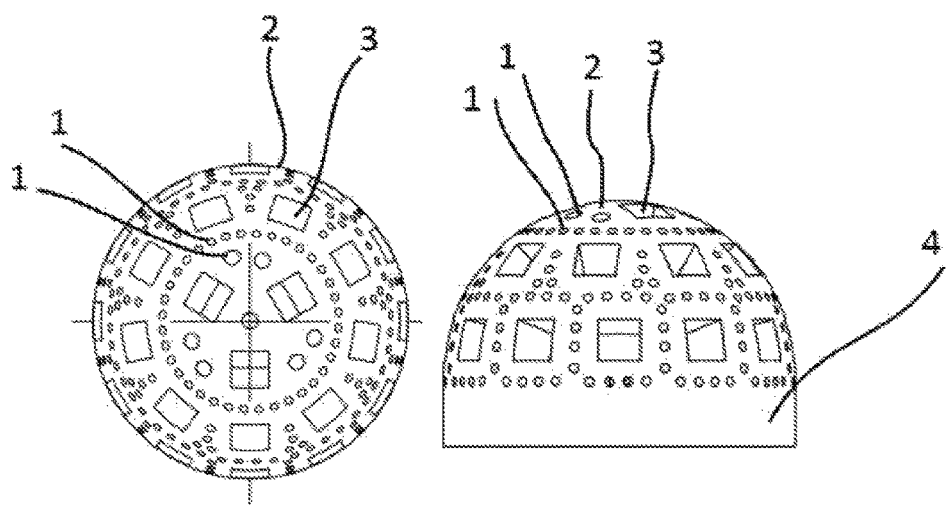
FIG. 3 illustrates another example realization of the hemispherical frame where the illumination channels are distributed on the available surface after the placement of the cameras, according to the invention.
Figure 4:
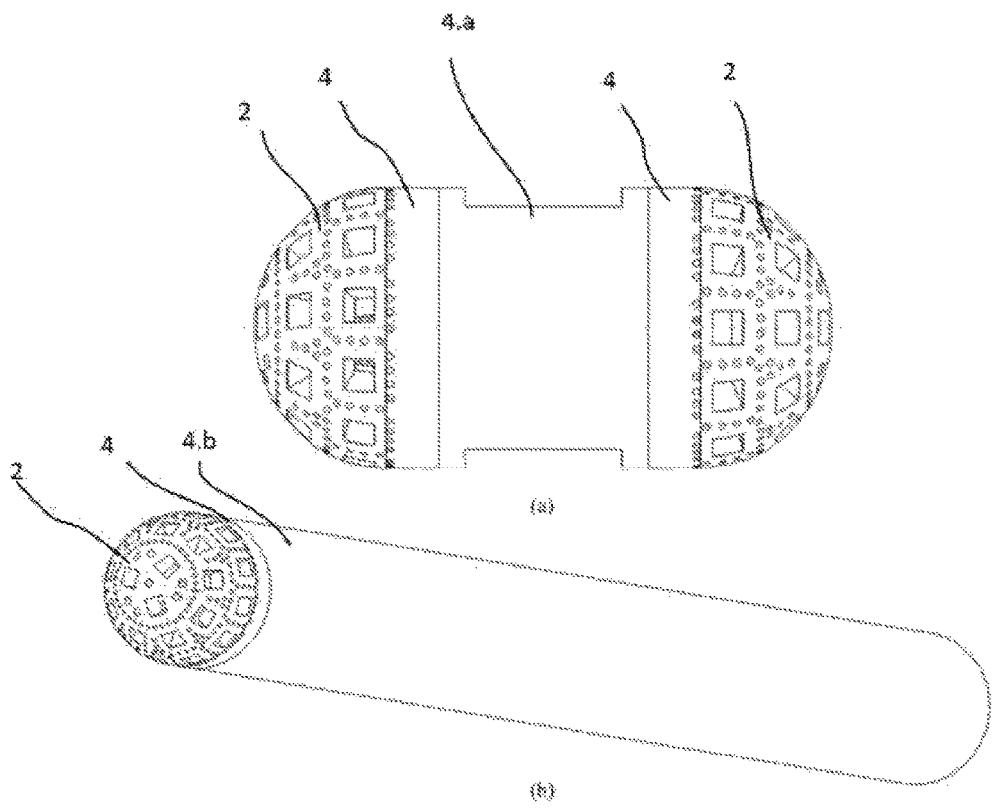
FIG. 4 shows a possible implementation for a different kind of endoscopic applications: (a) capsule type with two devices on the tips of an endoscopic capsule, the body of the capsule becomes the cylindrical part, and (b) surgical type with a long support as the cylindrical part.

The intensity value of each pixel is a combination of sampled intensity values of real image sensors of the imaging channels 3 placed on the hemispherical frame 2, which are illustrated in FIG. 3.

Each combination is based on a selection of the candidate intensity values of the real image sensors of the imaging channels 3 on the hemispherical mechanical frame 2.

A Bayer Pattern representation of the images is used during the selection of the intensity value candidates for each combination to generate each panoramic pixel intensity value. Any Bayer pattern sequence as described in [2] may be accepted as image sensors' Bayer pattern images.

The selection of intensity values for each combination is determined by the trigonometric relation of the final panorama pixel viewing direction and the real image sensor sampling direction.

The panorama pixel viewing direction is defined as a vector starting from the centre of the hemispherical mechanical frame 2 and directed trough a point in the space at infinite proximity.

Each panorama pixel direction should be unique and should not be coincident.

Each imaging channel's 3 viewing direction is determined by using its placement and orientation on the hemispherical mechanical frame 2.

If needed precise relative direction vectors of all the imaging channels 3 with respect to the hemispherical mechanical frame 2 centre may be determined afterwards by using a calibration process as defined in [ref1].

The Bayer Pattern Panorama is demosaiced afterwards and converted to a full colour image by using any means of interpolation method, preferably one that takes into account the object boundaries in the image.

REFERENCES

[ref1] "http://www.vision.caltech.edu/bougetj/calib_doc/"

RELATED PATENT PUBLICATIONS

[1] WO2012056437A1 Omnidirectional sensor array system
[2] U.S. Pat. No. 3,971,065A Color imaging array
[3] U.S. Pat. No. 5,657,073A "Seamless multi-camera panoramic imaging with distortion correction and selectable field of view"
[4] U.S. Pat. No. 5,425,123A "Multifiber Endoscope with Multiple Viewing Modes Free of Fixed Pattern Noise"
[5] U.S. Pat. No. 5,776,049A, "Stereo endoscope and stereo endoscope imaging apparatus"
[6] U.S. Pat. No. 6,997,871B2, "Multiple view endoscopes"
[7] U.S. Pat. No. 7,244,229B2, "Capsule endoscope"
[8] U.S. Pat. No. 7,662,093B2, "Reduced size imaging device"
[9] U.S. Pat. No. 7,869,856B2, "Encapsulated medical imaging device and method"
[10] U.S. Pat. No. 7,877,134B2, "Apparatus and methods for in vivo imaging"
[11] U.S. Pat. No. 8,382,658B2, "Capsule endoscope system"
[12] U.S. Pat. No. 8,414,474B2, "Multiple view angle endoscope apparatus"
[13] US20020114071A1, "Stereo endoscope"
[14] US20040254424A1, "Integrated panoramic and forward view endoscope"
[15] US20060217593A1, "Device, system and method of panoramic multiple field of view imaging"
[16] US20080045797A1, "Endoscope attachment and endoscope"
[17] US20080064923A1, "Device, system and method in-vivo analysis"
[18] US20090240108A1, "Capsule endoscopy system and method of controlling operation of capsule endoscope"
[19] US20110169931A1, "In-vivo imaging device with double field of view and method for use"
[20] US20110196200A1, "Multi-view endoscopic imaging system"
[21] US20120316392A1, "Spherical capsule video endoscopy"
[22] US20130109916A1, "Multi-camera endoscope"
[23] JP2006068109, "Spherical Capsule Type Omnidirectional Endoscope"
[24] EP2412290 "Endoscope and endoscope system"
[25] US2008084478 "System and method for an in-vivo imaging device with an angled field of view"
[26] U.S. Pat. No. 6,471,642 "Rigid endoscope optical system"
[27] US2005004474 "Method and device for imaging body lumens"
[28] U.S. Pat. No. 6,201,574 "Motionless camera orientation system distortion correcting sensing element"
[29] US2012242882 "Curved sensor camera with moving optical train"

The invention claimed is:

1. A multi-camera hemispherical very wide field of view imaging apparatus with omnidirectional illumination capability, the apparatus comprising:
a body;
a hemispherical mechanical frame arranged on an end of the body;
a plurality of imaging channels, each imaging channel including an image sensor and optics with a fixed focus for endoscopic imaging, the plurality of imaging channels being distributed over the hemispherical mechanical frame such that each imaging channel has a different viewing direction;
a central light source configured to provide light to the plurality of imaging channels; and
a control and processing circuit including a camera control unit, an illumination control unit, a sample and capture unit, and an image processing unit,
wherein each imaging channel includes a plurality of fiber optical illumination channels around a center of the respective imaging channel, each of the plurality of fiber optical illumination channels including a microfiber light guide having a determined angle of curvature arranged to transmit light from the central light source to an area outside of the hemispherical mechanical frame, and
wherein the camera control unit is configured to perform automatic gain compensation for each of the plurality of imaging channels, the illumination control unit is configured to perform automatic intensity dimming for each of the plurality of imaging channels, the sample and capture unit having an interface circuit for sampling, extraction and capturing frames of individual imaging channels, and the image processing unit is configured generate a spherical panoramic image by applying an algorithm.

2. The multi-camera apparatus of claim 1, wherein the control and processing circuit further includes an output interface, the output interface is configured to output the spherical panoramic image to a system, the system configured to visualize the spherical panoramic image.

3. The multi-camera apparatus of claim 1, wherein the body is cylindrical.

4. The multi-camera apparatus of claim 1, wherein the central light source is arranged center-down at a back part of the plurality of imaging channels and inside or at the end of the body.

5. The multi-camera apparatus of claim 1, wherein for each fiber optical illumination channel that is associated with the respective imaging channel, a light exit face of the microfiber light guide is arranged at a side of a respective opening for the imaging channel on the hemispherical mechanical frame.

6. The multi-camera apparatus of claim 1, wherein each imaging channel includes at least four fiber optical illumination channels, a light exit face of the microfiber light guide of the at least four fiber optical illumination channels arranged at a middle of a side of a respective opening for the imaging channel on the hemispherical mechanical frame.

7. The multi-camera apparatus of claim 1, wherein light exit faces of the microfiber light guide of the plurality of fiber optical illumination channels are arranged in rows between adjacent imaging channels.

8. The multi-camera apparatus of claim 7, wherein the rows are arranged to surround each opening for the plurality of imaging channels on the hemispherical mechanical frame.

9. The multi-camera apparatus of claim 1, wherein light exit faces of the microfiber light guide of the plurality of fiber optical illumination channels are arranged at a spherical surface of the hemispherical mechanical frame.

10. The multi-camera apparatus of claim 1, wherein each light exit face of the microfiber light guide of the plurality of fiber optical illumination channels are arranged on a spherical surface of the hemispherical mechanical frame.

11. The multi-camera apparatus of claim 1, wherein a light beam of each microfiber light guide of the plurality of fiber optical illumination channels has a different illumination angle.

* * * * *